United States Patent [19]

Katz et al.

[11] Patent Number: 4,855,445

[45] Date of Patent: Aug. 8, 1989

[54] SUBSTITUTED-8-ALKENYL-1,3,4,9-TETRAHYDROPYRANO(3,4-B)INDOLE-1-ACETIC ACIDS

[75] Inventors: Alan H. Katz, Lawrenceville; Christopher A. Demerson, Plainsboro, both of N.J.

[73] Assignee: American Home Products Corporation, New York, N.Y.

[21] Appl. No.: 294,705

[22] Filed: Jan. 9, 1989

Related U.S. Application Data

[62] Division of Ser. No. 201,010, Jun. 1, 1988, Pat. No. 4,822,781.

[30] Foreign Application Priority Data

Oct. 8, 1987 [CA] Canada .................................... 548883

[51] Int. Cl.$^4$ .......................................... C07D 209/12
[52] U.S. Cl. ............................................... 548/432
[58] Field of Search ................... 548/432, 508; 558/54; 568/937, 938; 564/314, 417, 250

[56] References Cited

U.S. PATENT DOCUMENTS

| | | | |
|---|---|---|---|
| 3,843,681 | 10/1974 | Demerson et al. | 548/432 |
| 3,939,178 | 2/1976 | Demerson et al. | 548/432 |
| 3,974,179 | 8/1976 | Demerson et al. | 548/432 |
| 4,585,877 | 4/1986 | Demerson et al. | 548/432 |
| 4,785,015 | 11/1988 | McKittrick et al. | 548/432 |

OTHER PUBLICATIONS

R. Morrison et al., Organic Chemistry, Second edition, p. 156, Allyn and Bacon, Boston (1967).

*Primary Examiner*—Mary E. Ceperley
*Attorney, Agent, or Firm*—Walter Patton

[57] ABSTRACT

Indole derivatives characterized by having a 1,3,4,9-tetrahydropyrano[3,4-b]indole-1-acetic acid nucleus bearing substituents in position 1-,5-,6-, 7- and 8-are disclosed. The derivatives are useful anti-inflammatory and/or analgesic agents. Methods for their preparation and use are also disclosed.

5 Claims, No Drawings

SUBSTITUTED-8-ALKENYL-1,3,4,9-TETRAHYDROPYRANO(3,4-B)INDOLE-1-ACETIC ACIDS

This is a division of application Ser. No. 201,010, filed June 1, 1988, now U.S. Pat. No. 4,822,781.

BACKGROUND OF THE INVENTION a. Field of Invention

This invention relates to novel indole derivatives, and to the processes for their preparation and use.

Notwithstanding the advances made during the last four decades in the development of agents for the treatment of inflammatory conditions and/or for analgesic purposes in conditions which require relief from pain in a mammal, there still remains a need for effective agents without the side effects associated with the therapeutic agents presently used for these purposes.

More specifically, this invention relates to tricyclic acetic acid derivatives in which the tricyclic portion thereof is characterized by having an indole portion fused to a pyrano ring. Still more specifically, the compounds of this invention are characterized as derivatives of the following tricyclic acetic acid system:

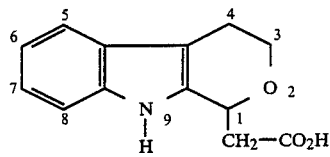

1,3,4,9-tetrahydropyrano[3,4-b]indole-1-acetic acid in which the carbons at the 1-, 5-, 6-, 7-, and 8-positions are further substituted.

The indole derivatives of this invention have been found to exhibit useful pharmacodynamic properties without eliciting undesirable side effects. Notable attributes of this effect are anti-inflammatory and/or analgesic activities.

b. Prior Art

The closest prior art to the present invention is:

Demerson et al, U.S. Pat. No. 3,939,178. Demerson et al disclosed 1,3,4,9-tetrahydropyrano[3,4-b]indoles and 1,3,4,9-tetrahydrothio-pyrano[3,4-b]indoles having analgesic and anti-inflammatory activity but not with the substituents of the present invention. McKittrick et al, Canadian Patent Application No. 530,253, filed Feb. 20, 1987 corresponding to U.S. Pat. No. 4,785,015. Hughes et al, U.S. Ser. No. 876,522, filed June 19, 1986, now abandoned. Related United States Patents are U.S. Pat. Nos. 3,974,179; 3,843,681 and U.S. Ser. No. 838,510, filed Mar. 11, 1986, now U.S. Pat. No. 4,670,462.

SUMMARY OF THE INVENTION

The compounds of this invention are represented by formula (I)

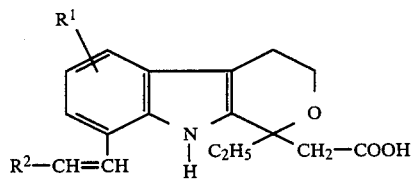

wherein $R^1$ is hydrogen, lower alkyl containing 1 to 4 carbon atoms or halogen; $R^2$ is lower alkyl containing 1 to 4 carbon atoms and the pharmaceutically acceptable salts thereof.

A preferred aspect of the present invention is the compounds represented by formula (I) wherein $R^1$ is hydrogen or fluorine; $R^2$ is methyl and the pharmaceutically acceptable salts thereof.

The most preferred compounds of the present invention are designated (Z)-1-ethyl-7-fluoro-1,3,4,9-tetrahydro-8-(1-propenyl)-pyrano[3,4-b]indole-1-acetic acid; and (Z)-1-ethyl-1,3,4,9-tetrahydro-8-(1-propenyl)-pyrano[3,4-b]indole-1-acetic acid.

The indole derivatives of this invention of formula (I) are prepared by the following process.

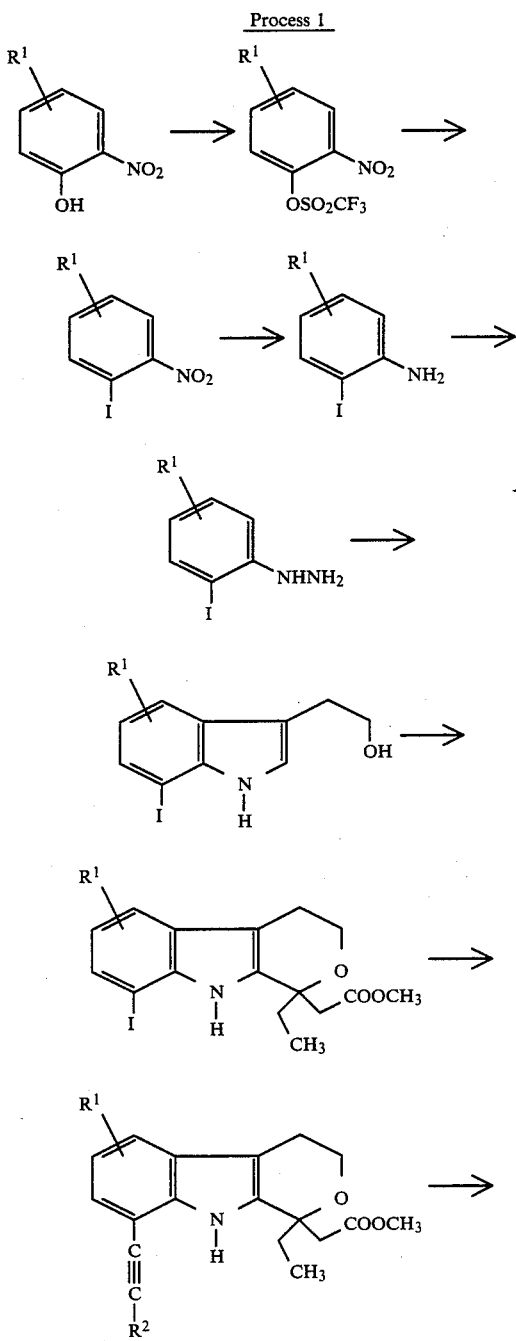

-continued
Process 1

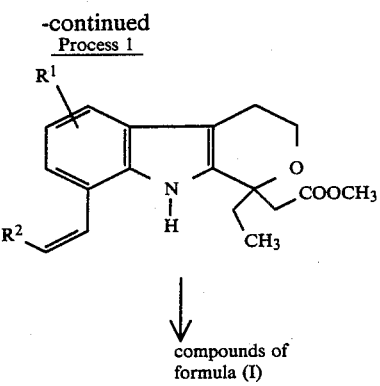

↓ compounds of formula (I)

DETAILED DESCRIPTION OF THE INVENTION

The term "lower alkyl" as used herein represents straight chain alkyl radicals containing 1 to 4 carbon atoms and branched chain alkyl radicals containing three to four carbon atoms and includes methyl, ethyl, propyl, isopropyl, butyl, isobutyl and the like.

The term "halogen" as used herein includes fluorine, chlorine, bromine and iodine.

The compounds of formula (I) form salts with suitable pharmaceutically acceptable inorganic and organic bases. These derived salts possess the same activities as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. The preferred salt is the sodium salt. Suitable organic bases include the following amines; lower mono-, di- and tri-alkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. The preferred salt is the 1,2-ethanediamine salt. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of salts of inorganic bases, it is preferred to dissolve the acid of formula (I) in water containing at least one equivalent amount of a hydroxide, carbonate, or bicarbonate. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid salt if that form is desired.

To produce an amine salt, the acid of formula (I) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Also included in this invention are the optical isomers of the compounds of formula (I) which result from asymmetric centers, contained therein e.g. 1-carbon. Such isomers can be obtained in substantially pure form by classical separation techniques and by stereochemically controlled syntheses.

ANTI-INFLAMMATORY ACTIVITY

The useful anti-inflammatory activities of the pyranoindole acetic acid derivatives of formula (I) are demonstrated in standard pharmacologic tests, for example, the test designated: Preventative Adjuvant Edema The objective of this test is to determine the ability of test drugs to exhibit an acute anti-inflammatory effect in rats. This test is a primary screen for anti-inflammatory drugs.

Species:

Male Sprague Dawley rats (180–200 g) are used. The animals have free access to water but food is withdrawn 18 hours before testing.

Drug Preparations and Adminstration:

Freund's complete adjuvant is prepared by suspending 5 mg of killed and dried *Mycobacterium butyricum* (Difco) in 1 mL mineral oil. The test compounds are dissolved, or suspended in 0.5% Tween 80 in distilled water according to their solubility. For primary screening all drugs are administered by gastric lavage at the arbitrary dosage of 25 mg/kg, p.o. in a volume of 0.5 mL/100 g body weight to groups of 10 animals.

Methodological Details:

The method is essentially that described by Wax et al, J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (days 0, 1 and 2). The injected hind paw volume is measured before the injection of adjuvant and 24 hrs. after the last drug administration (day 3) by means of a plethysmometer (Buxco Electronics Inc.). The difference between the hind paw volume on day 0 and day 3 represents the edema volume. Etodolac (25 mg/kg, p.o.) is included as a positive control.

Presentation of Results:

The mean edema volume (expressed as mL±SEM) is calculated for each group and the percentage protection conferred by the drug is calculated:

$$\% \text{ protection} = \frac{(c - t)\, 100}{c}$$

where c is the mean edema volume for the vehicle-treated (0.5% Tween 80 in distilled water) controls and t is the mean edema volume for the drug treated group.

ANALGESIC ACTIVITY

A further test used to determine the utility of the compounds of the present invention is designated: Drug Effects on Phenylbenzoquinone-induced Writhing in Mice The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g). The animals are fasted for 18 hours prior to use but have free access to water.

Drug Preparation and Administration:

Drugs are dissolved or suspended according to their solubility in 0.5% Tween 80 in distilled water. They are administered by gastric gavage in a volume of 5 mL/kg. For primary screening all drugs are administered at the arbitary dosage of 25 mg/kg, p.o. to a group of 10 mice.

Methodological Details:

A modification of the method of Siegmund et al, Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhing or abdominal squirming movements made by each mouse during the following 15 min. period is counted. The experiment is repeated with another group of 5 mice and the mean numbr of writhes per mouse for a group of 10 mice is calculated.

Presentation of Results:

Drug treated and vehicle-treated control groups are compared and the percentage protection conferred by the drug is calculated:

$$\text{Percentage protection} = \frac{(c - t)\, 100}{c}$$

where c = mean number of writhes in the control group
where t = mean number of writhes in the test drug group Typical results obtained for the compounds of the present invention in the aforementioned tests are as follows:

TABLE I

Substituted 1,3,4,9-Tetrahydropyrano[3,4-b]indole-1-acetic Acids

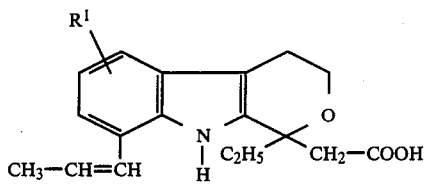

| Example | Preventative Adjuvant Edema* | Phenylquinone Writhing in Mice* |
|---|---|---|
| 1 | 69(10) | 32(10) |
| 2 | 73(25) | 11(200) |

*The numbers quoted are percent inhibition at the dose in mg/kg given in parentheses. See Table II for definition of $R^1$.

The lack of side effects associated with the compounds of this invention are demonstrated by standard acute toxicity tests as described by R. A. Turner in "Screening Methods in Pharmacology," Academic Press, New York and London, 1965, pp. 152–163, and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are adminstered orally in the form of solutions in suitable vehicles such as vegetable oils or water. The compounds of this invention may be administered orally in sustained release dosage form or transdermally in ointments or patches.

The compounds of this invention may also be administered in the form of suppositories.

The dosage of the compounds of formula (I) of this invention will vary with the particular compound chosen and form of administration. Furthermore, it will vary with the particular host under treatment. Generally, the compounds of this invention are administered at a concentration level that affords efficacy without any deleterious side effects. These effective anti-inflammatory and analgesic concentration levels are usually obtained within a therapeutic range of 1.0 μg to 500 mg/kg per day, with a preferred range of 1.0 μg to 100 mg/kg per day. The preferred anti-inflammatory and analgesic dose range is 20 μg to 20 mg/kg/day.

The compounds of this invention may be administered in conjunction with nonsteroidal anti-inflammatory drugs such as acetaminophen, ibuprofen and aspirin and/or with opiate analgesics such as codeine, oxycodone and morphine together with the usual doses of caffeine. When used in combination with other drugs, the dosage of the compounds of the present invention is adjusted accordingly.

The compounds of the present invention also possess antipyretic activity.

The following examples further illustrate this invention.

EXAMPLE 1

(Z)-1-Ethyl-7-fluoro-1,3,4,9-tetrahydro-8-(1-propenyl)-pyrano[3,4-b]indole-1-acetic Acid, 1,2-Ethanediamine Salt (I, $R^1$ = 7-fluoro)

Step (1) Preparation of 2-Fluoro-6-nitrophenyl Trifluoromethanesulfonate

A mixture consisting of 2-fluoro-6-nitrophenol (20 g, 0.14 mol) and potassium carbonate (20 g, 0.14 mol) in acetone (350 mL) was stirred at room temperature for 20 minutes. A solution of trifluoromethanesulfonyl chloride (23.7 g, 0.14 mol) in acetone (100 mL) was added dropwise at room temperature. Stirring was continued for 3 hours. The reaction was filtered, and the filtrate was concentrated. The residue was dissolved in diethyl ether (300 mL), washed with 0.1N NaOH, water, dried ($MgSO_4$), filtered and evaporated to give 21.5 g of the title compound.

$^1$H NMR ($CDCl_3$): δ 8.0 (m, 1H), 7.6 (m, 2H).

Step (2) Preparation of 2-Iodo-3-fluoronitrobenzene

A mixture consisting of 2-fluoro-6-nitrophenyl trifluoromethanesulfonate (62.0 g, 0.215 mol), lithium iodide (60 g, 0.451 mol) and 1-methyl-2-pyrrolidinone (400 mL) was heated with stirring at 130°-132° C. (oil bath temperature) for 18 hours. Upon cooling it was poured into water (1200 mL) and extracted with diethyl ether. The combined extracts were washed with 1N NaOH, water and with brine. The solution was dried ($MgSO_4$), filtered, and concentrated in vacuo to give 27.0 g of the title compound as a brown-colored solid title compound (m.p. 54°-57° C.).

$^1$H NMR ($CDCl_3$): δ 7.63 (d, J=8.1, 1H), 7.50 (m, 1H), 7.35 (m, 1H).

Step (3) Preparation of 2-Iodo-3-fluoroaniline Hydrochloride

A solution of 2-iodo-3-fluoronitrobenzene (27.0 g, 0.101 mol) in tetrahydrofuran (200 mL) was added dropwise over a 10 minute period to a stirring solution of stannous chloride dihydrate (68.0 g, 0.302 mol) in concentrated hydrochloric acid (200 mL). After 3 hours at room temperature the reaction was poured onto ice, made alkaline (pH 11) with 50% NaOH, and extracted with diethyl ether. The combined organic phases were washed with water, brine, dried ($MgSO_4$), filtered, and concentrated to almost dryness. Ethereal HCl was added pH 1-2), and the resulting precipitate filtered and dried to afford 25.0 g of the title compound, m.p. 197°-198° C. (dec.).

$^1$H NMR (DMSO-$d_6$): δ 7.09 (m, 1H), 6.6 (d, J=8.2, 1H), 6.4 (m, 1H).

Step (4) Preparation of 3-Fluoro-2-iodophenylhydrazine Hydrochloride

2-Iodo-3-fluoroaniline hydrochloride (5.7 g, 0.021 mol) was stirred in 7.4 mL of concentrated HCl and cooled to −10° C. An aqueous solution of sodium nitrite (1.63 g, 0.024 mL) in 5 mL water was added dropwise over a 20 minute period, stannous chloride (9.95 g, 0.044 mol) in 12 mL of 6N HCl added at −5° C., warmed to room temperature and stirring continued for 4 hours. The reaction mixture was cooled to 0° C., and made basic with 50% NaOH (pH 10-11), extracted with ether, washed with water, brine, dried ($MgSO_4$), filtered and concentrated to give the hydrazine. Addition of ethereal HCl (pH 1-2) gave 4.6 g of the title compound, m.p. 165°-167° C.

$^1$H NMR (DMSO-$d_6$): δ 10.35 (bs), 7.9 (bs), 7.4 (m, 1H), 6.88 (m, 1H), 6.78 (m, 1H).

Step (5) Preparation of 7-Iodo-6-fluorotryptophol

3-Fluoro-2-iodophenylhydrazine hydrochloride (18 g, 0.62 mol) was dissolved in 10% aqueous THF (165 mL) and a solution of dihydrofuran (5.3 g, 0.075 mol) was added at 0° C. This mixture was stirred at −10° C. to room temperature for 2 hours. Ether was added to the reaction mixture and the organic phase washed with brine. Concentration of the ether layer afforded the hydrazone (18.0 g as an amber oil). Without further purification the hydrazone was suspended in ethylene glycol and zinc chloride (15.0 g, 0.11 mol) was added. The mixture was heated to 165°-170° C. for 2.5 hours, then cooled to room temperature and extracted with ether. The ether layers were washed (brine), dried ($MgSO_4$) and concentrated to yield an oil. This was purified via flash chromatography using 1:2 EtOAc:hexane to give the tryptophol as a yellow oil (5.6 g).

$^1$H NMR ($CDCl_3$): δ 8.60 (bs), 7.48 (dd, $J_1$=8.5, $J_2$=5.0, 1H), 7.13 (d, J=2.2, 1H), 6.90 (t, J=8.7, 1H), 3.90 (t, J=6.3, 2H), 2.99 (t, J=6.3, 2H).

Step (6) Preparation of 1-Ethyl-7-fluoro-8-iodo-1,3,4,9-tetrahydropyrano[3,4-b]indole-1-acetic Acid, Methyl Ester 7-Iodo-6-fluorotryptophol (5.6 g, 0.018 mol) was dissolved in $CH_2Cl_2$ (400 mL). To this was added methyl 3-methoxy-2-pentenoate (3.2 g, 0.022 mol) and bromotrifluoride etherate (1.0 mL). After stirring at room temperature for 40 minutes the mixture was diluted with 10% $NaHCO_3$. The $CH_2Cl_2$ layer was separated and dried ($MgSO_4$) to yield 5.5 g of the pyrano[3,4-b]indole product as an oil, which solidified on standing, m.p. 109°-111° C.

$^1$H NMR ($CDCl_3$): δ 9.3 (bs, 1H), 7.34 (dd, $J_1$=8.5, $J_2$=5.0, 1H), 6.86 (t, J=8.6, 1H), 4.0-3.92 (m, 2H), 3.76 (s, 3H), 2.99 (d, J=16.6, 1H), 2.92 (d, J=16.6, 1H), 2.79-2.69 (m, 2H), 2.17-1.98 (m, 2H), 0.82 (t, J=7.3, 3H).

Step (7) Preparation of 1-Ethyl-7-fluoro-8-(1-propynyl)-1,3,4,9-tetrahydropyrano[3,4-b]indole-1-acetic Acid, Methyl Ester A mixture of 1-ethyl-7-fluoro-8-iodo-1,3,4,9-tetrahydropyrano[3,4-b]indole-1-acetic acid, methyl ester (5.2 g, 0.012 mol), copper (I) methyl acetylide (3.05 g, 29.72 mmol), and 75 mL of dry pyridine was refluxed, under a flow of nitrogen, for 6 hours. The mixture was then poured into 100 mL of 1N HCl and the aqueous solution was extracted with ether (3×100 mL). The combined extracts were washed with 1N HCl (2×100 mL) and saturated NaCl (2×100 mL), dried over magnesium sulfate, filtered and concentrated to give the crude product. This material was purified by flash chromatography (20% ethyl acetate/hexane, silica gel) to give the pure acetylenic ester (2.5 g).

$^1$H NMR ($CDCl_3$): δ 9.14 (bs, 1H), 7.32 (dd, $J_1$=8.6, $J_2$=5.0, 1H), 6.8 (dd, $J_1$=8.7, $J_2$=10.3, 1H), 4.04-3.91 (m, 2H), 3.73 (s, 3H), 2.99 (d, J=16.3, 1H), 2.90 (d, J=16.3, 1H), 2.78-2.68 (m, 2H), 2.23 (s, 3H), 2.2-1.98 (m, 2H), 0.82 (t, J=7.3, 3H).

Step (8) Preparation of (Z)-1-Ethyl-7-fluoro-8-(1-propenyl)-1,3,4,9-tetrahydropyrano[3,4-b]indole-1-acetic Acid, 1,2-Ethanediamine Salt A mixture consisting of 1-ethyl-7-fluoro-8-(1-propynyl)-1,3,4,9-tetrahydropyrano[3,4-b]indole-1- acetic acid, methyl ester (2.8 g, 0.085 mol), methanol (250 mL) and Lindlar catalyst (0.5 g) was hydrogenated at atmospheric pressure. The reaction was monitored by TLC until only a trace of starting material remained. After 42 minutes the reaction was filtered, and concentrated to give 2.6 g of a thick oil. This oil was dissolved in methanol (150 mL) and 1N potassium hydroxide was added (15 mL). The mixture was refluxed for 4 hours, then cooled and acidified with concentrated 1N HCl, and the aqueous solution extracted with ether. The ether layers were washed (brine), dried (MgSO$_4$) and concentrated to give 2.2 g of a thick oil. A solution of ethylenediamine (0.416 g in 30 mL ether) was added to the oil in 30 mL of ether. Concentration gave a solid. Recrystallization of the solid from toluene afforded 1.9 g of the title compound, m.p. 156°–158° C.

EXAMPLE 2

(Z)-1-Ethyl-8-(1-propenyl)-1,3,4,9-tetrahydropyrano[3,4-b]indole-1-acetic Acid

Step (1) Preparation of 7-Iodotryptophol

To a suspension of 2-iodophenylhydrazine hydrochloride in dioxane (220 mL) and water (14 mL) was added a solution of 2,3-dihydrofuran (18.22 g, 0.26 mmol) in dioxane (20 mL). The addition took 15 minutes. The resulting yellow solution was heated at 95° C. for 3 hour at which time the solution had turned red and no starting material was detected by TLC analysis. The reaction mixture was added to ether (1.5 L) and a dark brown oil separated. The ether solution was decanted from the residue, dried (MgSO$_4$), filtered and evaporated to produce a red-brown oil (71.8 g). This material was chromatographed through silica gel (40% EtOAc/hexane) to produce a yellow oil which solidified upon standing (16.19 g), m.p. 69°–71° C.

NMR (CDCl$_3$): δ 8.25 (m, 1H), 7.60 (m, 2H), 7.00 (m, 2H), 3.90 (t, 2H), 2.95 (t, 2H), 1.85 (s, 1H).

Step (2) Preparation of 1-Ethyl-8-iodo-1,3,4,9-tetrahydropyrano[3,4-b]indole-1-acetic Acid, Methyl Ester 7-Iodotryptophol (17.57 g 61.2 mmol), methyl propionylacetate (9.55 g, 73.4 mmol) and p-toluenesulfonic acid (3.3 g) were dissolved in benzene (500 mL) and refluxed in a Dean-Stark apparatus for 3 hours. The mixture was concentrated in vacuo and the resulting oil was dissolved in ether, washed with saturated NaHCO$_3$ (2×100 mL), dried (MgSO$_4$), filtered and evaporated to produce a brown oil (19.89 g).

Step (3) Preparation of 1-Ethyl-8-(1-propynyl)-1,3,4,9-tetrahydropyrano[3,4-b]indole-1-acetic Acid, Methyl Ester A mixture of 1-ethyl-8-iodo-1,3,4,9-tetrahydropyrano[3,4-b]indole-1-acetic acid, methyl ester (5.93 g, 14.86 mmol), copper (I) methyl acetylide (3.05 g, 29.72 mmol), and 75 mL of dry pyridine was refluxed, under a flow of nitrogen, for 6 hours. The mixture was then poured into 100 mL of 1N HCl and the aqueous solution was extracted with ether. The combined extracts were washed with 1N HCl and saturated NaCl, dried over magnesium sulfate, filtered and concentrated to give the crude product. The material was purified by flash chromatography (15% ethyl acetate/hexane, silica gel) to give the pure title compound (2.16 g).

Step (4) Preparation of (Z)-1-Ethyl-8-(1-propenyl)-1,3,4,9-tetrahydropyrano[3,4-b]indole-1-acetic Acid, Methyl Ester A mixture of 1-ethyl-8-(1-propynyl)-1,3,4,9-tetrahydropyrano[3,4-b]indole-1-acetic acid, methyl ester (155 mg, 0.5 mmol), Lindlar catalyst (15 mg), and methanol (10 mL) was charged with 1 atmosphere of hydrogen and allowed to stir at room temperature overnight. The catalyst was then removed by filtration through a celite plug, and the filtrate concentrated to give 170 mg of the crude product. This material was purified by flash chromatography (10% ethyl acetate/hexane, silica gel) to give the pure title compound as yellow oil (70 mg).

Step (5) Preparation of (Z)-1-Ethyl-8-(1-propenyl)-1,3,4,9-tetrahydropyrano[3,4-b]indole -1-acetic Acid (Z)-1-Ethyl-8-(1-propenyl)-1,3,4,9-tetrahydropyrano[3,4-b]indole-1-acetic acid, methyl ester (1.01 g, 3.2 mmol) was dissolved in a mixture of 11.2 mL of ethanol and 11.2 mL of 10% aqueous sodium hydroxide, and the solution was heated under reflux for 3 hours. The reaction mixture was then concentrated to dryness, and a mixture of 13.4 mL of ether and 13.4 mL of 10% aqueous sodium hydroxide was added to the residue. The layers were separated, and the aqueous layer was acidified with concentrated hydrochloric acid and extracted with ether (2×25 mL). The combined ether extracts were dried over anhydrous magnesium sulfate, filtered and concentrated to give 897 mg of the crude product. This material was purified by flash chromatography (20% ethyl acetate/hexane, H$_3$PO$_4$ treated silica gel) to give the desired product as a colorless oil which partially solidified upon standing. Trituration with petroleum ether provided 440 mg of an off-white solid, m.p. 89.5°–93.5° C.

TABLE II

Substituted 1,3,4,9-tetrahydropyrano[3,4-b]indole-acetic Acids

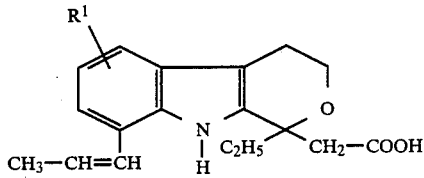

| Example | R$^1$ | Melting Point °C. |
|---|---|---|
| 1 (1,2-ethanediamine salt) | —F | 156–158 |
| 2 | —H | 89.5–93.5 |

We claim:

1. The process for producing the compounds having the structure

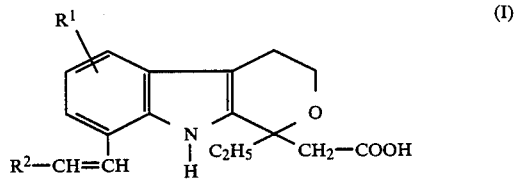

wherein R$^1$ is hydrogen, lower alkyl containing 1 to 4 carbon atoms or halogen; R$^2$ is lower alkyl containing 1 to 4 carbon atoms and the pharmaceutically acceptable salts thereof which comprises (a) successively triflating, heating with lithium iodide, and reducing the compound of structure

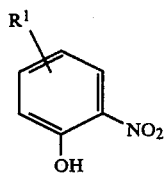

wherein $R^1$ is as defined above to produce the amine of structure

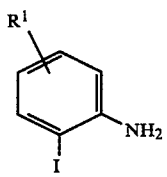

wherein $R^1$ is as defined above (b) reacting said amine with $HNO_2$ and $SnCl_2$ to produce the hydrazine of structure

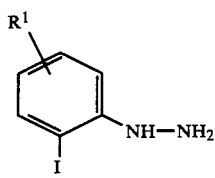

wherein $R^1$ is as defined above (c) reacting said hydrazine with dihydrofuran to produce the corresponding hydrazone and in the presence of zinc chloride converting the hydrazone to the corresponding tryptophol of structure

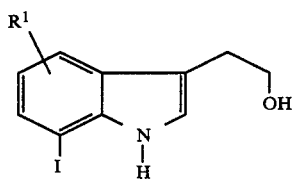

wherein $R^1$ is as defined above (d) cyclizing said tryptophol with methyl 3-methoxy-2-pentenoate in the presence of boron trifluoride etherate or with methyl propionyl acetate in the presence of p-toluenesulfuric acid to produce the indole of structure

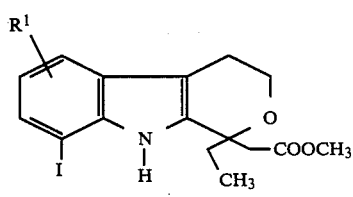

wherein $R^1$ is as defined above (e) reacting said indole with copper (I) alkyl acetylide to produce the ester of structure

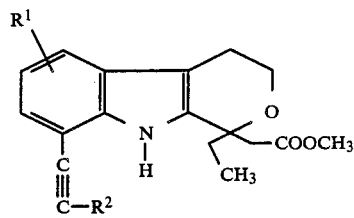

wherein $R^1$ and $R^2$ are as defined above (f) hydrogenating said propynyl derivative to produce the compound of structure

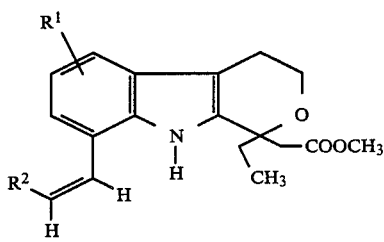

wherein $R^1$ and $R^2$ are as defined above (g) hydrolyzing said ester to produce the desired compound of structure (1) and optionally converting said compound to a phrmaceutically acceptable salt.

2. The process according to claim 1 in which in step (e) the compound of structure

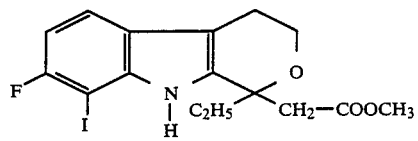

is alkylated with copper (I) methyl acetylide to produce the compound of structure

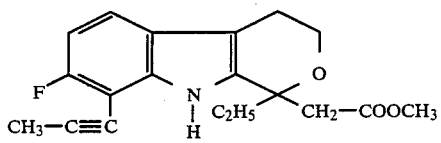

3. The process according to claim 1 in which in step (e) the compound of structure

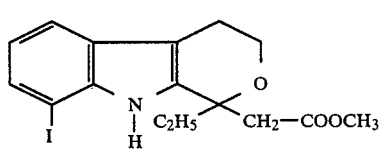

is alkylated with copper (I) methyl acetylide to produce the compound of structure

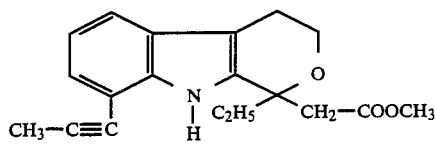
4. A process according to claim 1 in which in step (f) the compound of structure
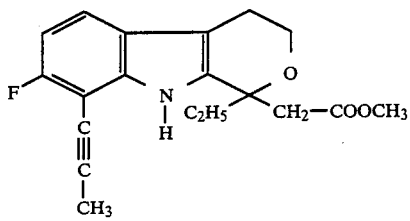
is hydrogenated using Lindlar catalyst to produce the compound of structure
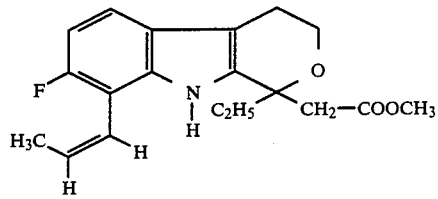
5. A process according to claim 1 in which in step (f) the compound of structure
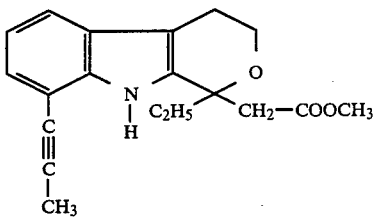
is hydrogenated using Lindlar catalyst to produce the compound of structure
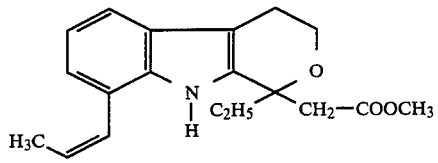
* * * * *